United States Patent
Pamplin

(10) Patent No.: US 10,433,771 B2
(45) Date of Patent: Oct. 8, 2019

(54) DEVICE FOR ASSESSING AND RECORDING POSTURE

(71) Applicant: James Christopher Pamplin, Thornton, NH (US)

(72) Inventor: James Christopher Pamplin, Thornton, NH (US)

(*) Notice: Subject to any disclaimer, the term of this patent is extended or adjusted under 35 U.S.C. 154(b) by 131 days.

(21) Appl. No.: 15/726,432

(22) Filed: Oct. 6, 2017

(65) Prior Publication Data

US 2019/0104971 A1    Apr. 11, 2019

(51) Int. Cl.
G06K 9/00 (2006.01)
A61B 5/11 (2006.01)
A61B 5/00 (2006.01)
A61B 5/053 (2006.01)
A61B 5/103 (2006.01)

(52) U.S. Cl.
CPC .......... *A61B 5/1128* (2013.01); *A61B 5/0004* (2013.01); *A61B 5/0077* (2013.01); *A61B 5/053* (2013.01); *A61B 5/0537* (2013.01); *A61B 5/4561* (2013.01); *A61B 5/7278* (2013.01); *A61B 5/103* (2013.01); *A61B 2576/00* (2013.01)

(58) Field of Classification Search
CPC combination set(s) only.
See application file for complete search history.

(56) References Cited

U.S. PATENT DOCUMENTS

| | | | |
|---|---|---|---|
| 2002/0061130 A1* | 5/2002 | Kirk | G06T 7/80 382/154 |
| 2002/0064305 A1* | 5/2002 | Taylor | G06T 11/60 382/154 |
| 2004/0202364 A1* | 10/2004 | Otani | G01B 21/042 382/154 |
| 2004/0223219 A1* | 11/2004 | Tooyama | G02B 27/2207 359/464 |
| 2012/0257017 A1* | 10/2012 | Pettersson | G01B 11/005 348/46 |
| 2017/0337701 A1* | 11/2017 | Jovanovich | G06T 7/74 |

* cited by examiner

*Primary Examiner* — Alex Kok S Liew
(74) *Attorney, Agent, or Firm* — Michael Persson; Catherine Napjuo; Chisholm Persson & Ball

(57) ABSTRACT

A posture assessment system including a base, a frame, a series of adjustable lasers disposed on the frame, a camera, and a software product that automatically receives information from the lasers and camera to provide a practitioner with a patient's posture assessment.

23 Claims, 4 Drawing Sheets

Receiving laser information 56

Receiving photograph 60

Receiving practitioner input 58

Producing posture assessment 74

Commanding camera to take photograph 70

Commanding lasers to switch on/off 72

Providing user interface 76

FIG. 3A

| Vital Signs | | | | | | |
|---|---|---|---|---|---|---|
| Height: ☐ inches | Temperature: ☐ F | Rt. Blood Pressure: Seated ☐ ☐ | Standing ☐ ☐ |
| Weight: ☐ lbs | Pulse Rate: ☐ bpm | Lt Blood Pressure: Seated ☐ ☐ | Standing ☐ ☐ |
| BMI: ☐ | Respiration Rate: ☐ bpm | | |

78

Mental Assessment
Status: ○ Normal ○ Confused ○ Incoherent
Mood: ○ Anxious ○ Calm ○ Depressed ○ Cooperative ○ Uncooperative ○ Angry

Appearance
Grooming: ○ Poorly Groomed ○ Well Groomed
Physique: ○ Normal ○ Slim ○ Muscular ○ Overweight ○ Obese

Posture  Coronal Plane                Sagital Plane              Transverse Plane
CS: ○Normal ○LT ○RT    CS: ○Normal [15] Foward    Ears: ☐ °elev ○Normal ○LT ○RT
TS: ○Normal ○LT ○RT    TS: ○Normal ○Hyper ○Hypo   Shlds: [1] °elev ○Normal ●LT ○RT
LS: ○Normal ○LT ○RT    LS: ○Normal ☐ Foward       Hips: ☐ °elev ○Normal ○LT ○RT

80

Gait
○ Limp ○ Cerebellar ataxia ○ Parkinsonian ○ Spastic ○ Hemiparesis ○ Scissor ○ Steppage

DEVICE FOR ASSESSING AND RECORDING POSTURE

FIELD OF THE INVENTION

The present invention relates to the field of diagnostic assessment, and in particular, to diagnostic assessment of human posture.

BACKGROUND

In many medical fields, particularly chiropractic, an assessment of a patient's posture is necessary. Some tools currently exist in relation to this necessity. A large, but easily deployable grid that provides visual clues to a person's posture is sold under the trademark POSTURE PRO, for example. This grid is merely an educational tool, however, and difficult to use in actual patient analysis.

Alternatively, a mobile app for posture assessment is sold under the trademark POSTURESCREEN by a company doing business as PostureCo. With this app, a practitioner takes a photograph of a patient. The app allows the practitioner to indicate certain points on the body of the patient within the photograph. The practitioner then adds the patient's gender, height and, optionally, weight. The app is then able to generate reports on the patient's posture. Although this product may be useful in assessing posture, it may be difficult for the practitioner to exactly pinpoint the correct body points on a photograph. As the distances and angles between these points are key to an accurate posture assessment, an inability to precisely locate these points may seriously skew the results, leading to inconsistent assessments and less effective treatments. Moreover, photographing the patient directly may make the patient uncomfortable or self-conscious. A more accurate and depersonalized system would improve over this system.

In addition, several posture assessment systems are sold under the trademark SAM by SAM, LLC. Each of these systems includes a base including a scale and frame extending upward from the scale. The frame has two sides extending vertically upward from either side of the base, a top piece that connects the two sides, and a fifth piece extending outward from one side of the top piece, parallel to the base. A practitioner strings three lines between the sides, one line between the top piece and the base, and one line between the fifth piece and the base. These strings represent normal posture or alignment. A patient then stands on the base and the practitioner then strings five lines of a different color from the "normal" lines across the sides and down between the top piece and fifth piece and the base. These lines indicate the posture or alignment of the patient. A photograph is then taken of the disparity between the normal lines and the lines of the patient and this photograph is used in assessing the patient's posture. It also may be used as a comparison against future similar assessments to track progress of a course of posture correction. Although these systems are useful, they include no automation of the derivation from "normal" and the product photographs may be subject to human error, e.g. poor photography skills or inconsistent photograph taking.

Another posture detection apparatus and method is disclosed in U.S. Pat. No. 5,886,788 to Kobayashi. The disclosed apparatus and method utilize a light source; an image data feeding means to feed the posture of a human body or its parts as image data; a spatial modulating means to modulate the amplitude distribution of a beam from the light source according to the image data fed by the image data feeding means; a data recording medium in which a plurality of reference images have been recorded; an optical means to focus the data bearing beam modulated by the spatial modulating means onto the data recording medium and a plurality of optical detecting means to analyze a beam emanating from the data recording medium at positions having different angles with respect to the data recording medium. Although this system may be effective at assessing posture, it is quite complicated, requiring, for example precision placement of laser oscillators, collimator lenses, and LCD panels. Such a system is fraught with the potential for human error and requires a great deal of sensitive and expensive hardware.

Another posture and weight distribution analyzer is disclosed in U.S. Pat. No. 6,387,061 to Nitto. This discloses a diagnostic apparatus employing a spaced grid and a centerline on a vertically mounted mirror to reflect the skeletal position of a patient. The patient stands on two scales which measure the weight borne by each of the patient's legs. The output of each scale is displayed on the mirror. An aperture is formed in the mirror to enable the patient to be photographed. The photograph may be printed on paper bearing the grid pattern and the centerline.

Although each of these analysis devices has merit for posture assessment, there is room for improvement. In particular, an easy-to-use, depersonalized, simple system, including inexpensive and easily replaceable parts, which automates results into a posture assessment is desired.

SUMMARY OF THE INVENTION

In its most basic form, the posture assessment system of the present invention includes a base with a center portion and right and left sides; a frame extending perpendicularly upward from the base with right and left sides, a top side, and an arm; a grid sheet hanging from the frame's top side whose width is entirely within the frame's left and right sides; first and second right and left side lasers and a top side laser, which are disposed around the frame and include laser adjustment means; a camera on the end of the arm; photograph transmission means for transmitting a photograph taken by the camera; and a software program that receives photographs taken by the camera, which includes laser positions in the preferred embodiment; practitioner input; and develops a posture assessment therefrom.

Before describing the system components in more detail, a description of how the system is used may be clarifying. A patient will step on the base so that he is standing between the right and left sides of the frame and under the top side, behind the grid sheet. In the patient's first position, the grid sheet hangs in front of the patient and the middle vertical line of the grid sheet is in line with the centerline of the patient's body, and the patient faces the grid sheet. The practitioner adjusts the height of the upper left side laser to correspond with the height of the patient's left shoulder; the height of the lower left side laser to correspond with the height of the patient's left hip; the height of the upper right side laser to correspond with the height of the patient's right shoulder; and the height of the lower right side laser to correspond with the height of the patient's right hip. The patient is present for these adjustments, so the practitioner can make sure the laser is hitting at exactly the correct heights on the patient for the posture assessment. The patient then steps away from the base. The camera takes a photograph of the lasers superimposed on the grid sheet. This photograph is transmitted to the software product. The practitioner directs the patient to step back on the base so the patient is facing the right or left side of the frame. The middle vertical line of the grid sheet in front of the patient should be aligned with the patient's ankle. The practitioner then directs the top laser down at an angle that intersects either the patient's ear and shoulder or the patient's shoulder and hip. The patient's measurements are thus finished. The patient again steps away from the base and the camera takes a photograph of the lasers superimposed on the grid sheet. This photograph is also transmitted to the software product. Photographs are never taken of the patient himself, but only of the lasers superimposed on the grid. This depersonalization not only makes the patient more comfortable, but also the practitioner who may proceed with the assessment without worrying about offending the patient through touching or bad photography, for example. Removing this human element therefore encourages both patient comfort and practitioner accuracy. The practitioner may enter further information about the patient, such as height and weight. Using the photograph and information input by the practitioner, the software product then produces a posture assessment. This assessment may be used by the practitioner to diagnose misalignments and other disorders and/or to develop a treatment plan for the patient.

The base is a simple platform on which the patient stands. The base may be made of wood, plastic, metal, or any other material sturdy enough to be stood upon and to support the frame. The right and left sides of the frame extend upward and perpendicularly from the right and left sides of the base, respectively. In some embodiments, the center portion and right and left sides are all one level base. In preferred embodiments, the right and left sides are raised from the center portion so as to more easily support the right and left sides of the frame extending therefrom. In some embodiments, the base includes a scale so that the patient's weight may be taken. The scale may be divided so that the patient's right and left halves may be weighed separately. In embodiments that include a scale, the system also includes weight transmission means for transmitting the weight (or weights) of the patient and the software product includes means for receiving the weight.

The frame includes at least right and left sides extending upward from the base's right and left sides, a top side connecting the right and left sides, and an arm extending perpendicularly outward from the top side such that it is parallel with the base and the floor. The frame is preferably made from a lightweight material, such as plastic or aluminum. In some embodiments, the system may include a device for measuring the patient's electrical impedance. The results of the electrical impedance would be used to determine the patient's body mass index. The device is preferably a handle made of conductive material that extends from the frame or the base and, when grasped by the patient, measures the patient's electrical impedance. Although this handle is preferred, one of at least ordinary skill in the art will recognize that there are many devices that may be included in the system that would measure the patient's electrical impedance. In embodiments that include a device for measuring the electrical impedance of the patient, the system also includes electrical impedance transmission means for transmitting the electrical impedance of the patient and the software product includes means for receiving the electrical impedance. The arm preferably extends from the center of the top side. The arm has an end that is the opposite side of its intersection with the top side. The camera is preferably disposed on the end of the arm. As discussed below, the camera will take a photograph of the lasers superimposed on the grid sheet. Although the arm holding the camera may be positioned other than extending from the center of the top side in order to effect such a photograph, the center position is preferable. The right and left sides of the frame have a height of at least six feet, so as to accommodate patients of different heights. In some embodiments the camera may use video to assess the patient's range of motion. In some embodiments, the camera includes camera adjustment means for positioning the direction of the camera's view.

In preferred embodiments, the top side is two crossbars between the right and left sides. In such embodiments, the first crossbar extends between the tops of the right and left sides and the second crossbar extends between the right and left sides a little lower than the first crossbar. The second crossbar is preferably zero to three inches below the first crossbar. In embodiments that include the first and second crossbars, it is preferred that the arm extend from the first crossbar and the top laser be disposed on the second crossbar. It is understood that in embodiments where the top side is a single crossbar, the arm extends from that single crossbar and the top laser is disposed on the single crossbar.

The grid sheet hangs from the top side of the frame. The grid sheet has a width that is slightly less than the distance between the right and left sides of the frame so that the entirety of the width of the grid sheet is visible between the left and right sides of the frame. The grid sheet includes a grid of vertical and horizontal lines. It preferably has a wide line down the center of the sheet and two bold lines on either side of the wide dark line halfway between the wide line and the vertical sides of the grid sheet. The grid sheet also includes a plurality of additional regularly spaced vertical lines parallel to the wide line and bold lines. The grid sheet also includes several bold horizontal lines spaced regularly down the length of the grid sheet. It also includes a plurality of additional regularly spaced horizontal lines parallel to the bold horizontal lines. All of the bold and additional horizontal lines are perpendicular to all of the wide, bold, and additional vertical lines. The grid sheet is made of any material that may hang like a sheet, as described, including paper, laminated paper, a cloth sheet, foldable ridged board, a metal sheet, or canvas. It is preferred that the grid sheet material be fairly robust so as not to tear during repeated use, especially set up and take down of the system.

Disposed upon each of the left and right sides of the frame includes an upper and a lower laser. At least one top laser is also disposed upon the top side of the frame. Although the left and right sides may include greater than two lasers each and the top side may include greater than one laser, it is preferred that each side include two lasers and the top side include only one laser. The upper and lower lasers required on the left and right sides of the frame correspond approximately to the patient's shoulder and hip heights. Additional lasers may be added that correspond to the patient's ankle, knee, or ear heights, for examples. Alternatively, depending on the patient's problem area(s), the two required upper and lower lasers may be adjusted to measure different body parts than the shoulders and hips.

Each laser includes laser adjustment means for adjusting where the laser points. For the lasers disposed on the right and left sides of the frame, the adjustment means preferably allow the entire laser to be moved up and down along the frame sides to a different location along the frame sides. This allows the lasers to hit the right height along the body of patients of different heights. The desired place along the frame for the lasers to be positioned for a specific patient is referred to herein as the "location" of the laser. The top laser is preferably disposed on the top side halfway between the two sides of the frame. The laser adjustment means for the top laser include at least two types of adjustment. The top laser may be moved horizontally to the left and right along the crossbar on which is it disposed. Again, this linear preferred placement is the location of the top laser. Once the top laser is in the preferred location, i.e. the middle of the patient's head, the top laser may also be adjusted through a range of angles, with one extreme being, for example, the laser being approximately collinear with the plane of the vertical lines of the grid sheet or at approximately a 0° angle from the grid sheet, and the other extreme being, for example, the laser pointing away from and behind or in front of the grid sheet to create as much as an 80° angle with the plane of the vertical lines of the grid sheet. As used herein, this adjustment of the top laser to any of the angles within this range is referred to as "angling through a range." For each of the laser adjustment means, whether these are adjusting the left and right side lasers up and down; adjusting the top laser right and left; or angling the top laser through a range, one of at least ordinary skill in the art will recognize that there are many ways to achieve such adjustment, such as manually with screws that may be loosened for the adjustment and tightened once the preferred position and/or angle is attained; robotics or actuators that make the adjustment in a more automated fashion; or any other means commonly used in the art. Each of these common means to achieve the various adjustments described above is contemplated as being included within the scope of the present invention.

In some embodiments the system may also include laser transmission means for transmitting information about the positions of the various lasers. This information will include the location of the various lasers on their respective parts of the frame, as well the angle within the range at which the top laser is positioned. In some embodiments, this information is transmitted wirelessly to the software product of the system, discussed below. In other embodiments, each laser is physically wired and the transmission of the information is through the wires or cables. In embodiments that include physical wiring for information transmission, the system may also include a hub where each of the laser's respective wires meet. The hub may condense these multiple wires into a single cable. As discussed below, the positions of the lasers is preferably gleaned through the software means for receiving the photograph. In other words, the locations of the lasers are taken from the photograph, rather than as described above through separate laser transmission means, although this is an option.

As discussed above, the camera is preferably disposed on the end of the arm, which extends from the center of the top side. The camera will take a photograph of the lasers superimposed on the grid. The system includes photograph transmission means for transmitting these photographs to the software product. The photograph also indicates the locations of the lasers, so the photograph transmission means may also transmit the locations of the lasers. These transmission means may be wireless or wired. In embodiments that include wired photograph transmission means and a hub, the photograph transmission means wire may route through the hub. Later, once the photographs of the lasers are transmitted to the software product, the software product will superimpose the lasers onto a depersonalized human image with normal posture. The comparison of the superimposed lasers specific to the patient's posture over the human image with normal posture will illustrate the significance of the patient's postural difference from normal.

Finally, the system includes a software product. This software product may be downloadable from a physical disc or from the internet onto a hard drive of a computing device, such as a laptop computer, a desktop computer, a tablet, or a mobile phone. It may also be used without downloading, through an app using the Internet, for example. The software product is able to at least receive photographs taken by the camera; receive input from the practitioner about the patient; superimpose the photographs of the lasers onto a depersonalized human image with normal posture; and produce a posture assessment based on all of this information that it may receive. In the preferred embodiment of the software product, receiving the photographs also entails receiving the locations of the lasers, as the lasers' locations will be indicated in the photograph. In embodiments that include laser transmission means, however, the software product is also adapted to receive information regarding the positions of the lasers directly. The software product may also issue commands to the camera to take a photograph and/or to switch the lasers on or off. In preferred embodiments of the software program, the software program also provides a user interface indicating information gathered and entered and/or displaying the superimposed lasers on the depersonalized human image with normal posture.

In its most basic form, a method of the present invention includes the following steps using the system of the present invention as described above: positioning a patient standing on the base and facing the grid sheet; adjusting the upper left laser to a height of the patient's left shoulder; adjusting the lower left laser to a height of the patient's left hip; adjusting the upper right laser to a height of the patient's right shoulder; adjusting the lower right laser to a height of the patient's right hip; removing the patient from the base; taking a photograph of the grid sheet with the lasers superimposed thereon; transmitting the photograph to the software product, including the locations of the lasers in the preferred embodiment; receiving the positions the photograph, including the lasers' locations in the preferred embodiment; producing a posture assessment; positioning the patient facing the right or left side; adjusting the top laser so as to bisect the patient's ear and shoulder or shoulder and hip; removing the patient from the base; taking a photograph of the grid sheet with the lasers superimposed thereon; transmitting the photograph to the software product; receiving the photograph from the software product; and producing a posture assessment. Additional steps may include receiving the laser locations and the angle of the top laser through the laser transmission means; receiving input from the practitioner about the patient, such as gender, height, and weight; developing a treatment plan based on the posture assessment; undergoing the treatment plan; and repeating the steps of the basic method for the purpose of comparing previous posture assessments. These last additional steps will inform the practitioner as to whether a treatment plan is working to correct any misalignments indicated by the original posture assessment.

These aspects of the present invention are not meant to be exclusive and other features, aspects, and advantages of the present invention will be readily apparent to those of ordinary skill in the art when read in conjunction with the following description and accompanying drawings.

BRIEF DESCRIPTION OF THE DRAWINGS

FIG. 2 is a block diagram indicating functionality of the software product of the system of the present invention.

FIGS. 3A and 3B are screenshots of an optional user interface function of the software product of the present invention.

DETAILED DESCRIPTION

Figure 1:
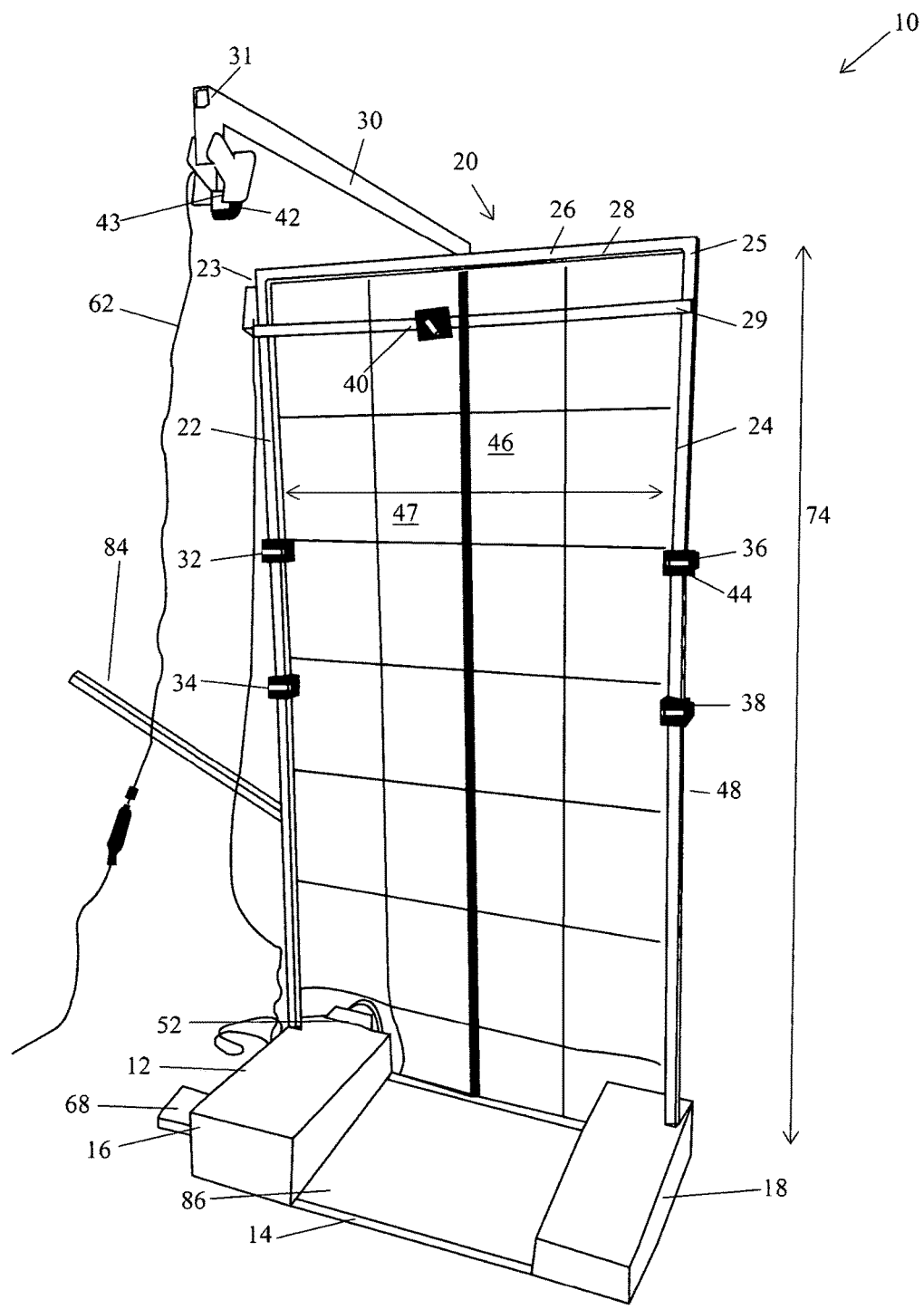
FIG. 1 is a perspective view of the system of the present invention.

Referring first to FIG. 1, system 10 of the present invention is shown in perspective. System 10 includes base 12 with center portion 14, left side 16, and right side 18; frame 20 with left side 22, right side 24, top side 26, and arm 30; and grid sheet 46. In the preferred embodiment shown, top side 26 is divided into first crossbar 28, from which arm 30 extends, and second crossbar 29 on which top laser 40 is disposed. First crossbar 28 extends between tops 23, 25 of left and right frame sides 22, 24 respectively. Second crossbar 29 is disposed 0-3" below first crossbar 28. It is understood that some embodiments only include one crossbar that is the top side 26, and arm 30 extends from this one crossbar and top laser 40 is disposed on this one crossbar.

Left and right sides 22, 24 of frame 20 extend up perpendicularly from left and right sides 16, 18 of base 12. Left and right sides 22, 24 have a height 74 of at least 6', so as to accommodate patients of varying heights. Upper and lower left side lasers 32, 34 are disposed on left side 22 of frame 20. Upper and lower right side lasers 36, 38 are disposed on right side 24 of frame 20. Top laser 40 is disposed on top side 26. In the preferred embodiment shown, top laser 40 is disposed on second crossbar 29 of top side 26.

Grid sheet 46 hangs from top side 26 (first crossbar 28 in this embodiment). As shown, grid sheet 46 includes a grid of horizontal and vertical lines, some of which are emboldened and/or wider than others. Generally, the patient is positioned with reference to the center, widest line. Grid sheet 46 has a width 47 that is entirely contained within left and right frame sides 22, 24.

Camera 42 is disposed on the end 31 of arm 30. Camera 42 may include camera adjustment means 43 for adjusting a position of camera 42, specifically the angle of the view with respect to the grid. System 10 also includes photograph transmission means 62 for transmitting photographs taken by camera 42 to software product 54. In the preferred embodiment shown, the photograph transmission means 62 are physical wires. It is understood that the photograph transmission means 62 may also be wireless or any other such means commonly used in the art. In some embodiments camera 42 may use video to assess the patient's range of motion.

System 10 may include hub 52 where power cords of laser transmission means 44 and/or photograph transmission means 62 may be gathered and consolidated. System 10 may also include switches 68, for turning the lasers on and off. System 10 may also include device 84 for measuring the electrical impedance of the patient. The preferred embodiment of device 84 is a handle, as shown, extending from frame 20 or base 12, which the patient may grip while standing on base 12. System 10 may also include scale 86, which is incorporated into base 12, and may include the capability to weigh each side of the patient.

Now referring to FIG. 2, a block diagram indicating functionality of software product 54, which is part of system 10, is provided. The most basic embodiment of software product 54 has the following functions: receiving photographs 60 taken by camera 42, through photograph transmission means 62; receiving practitioner input 58 about the patient, such as their gender, height, and weight; superimposing the photographs of the lasers onto a depersonalized human image with normal posture 63; and producing a posture assessment 74. The purpose of system 10 is to assess a patient's posture. This last function of producing a posture assessment 74 is the product and goal of system 10. Indicated in dashed boxes are additional functions of software product 54 provided in some embodiments of system 10: commanding the camera to take a photograph 70; commanding lasers to switch on and/or off 72; providing a user interface 76; and receiving laser information 56 from laser transmission means 48. The functions 70, 72 may be achieved manually, which is why they are optional functions for software product 54.

Figure 3B:
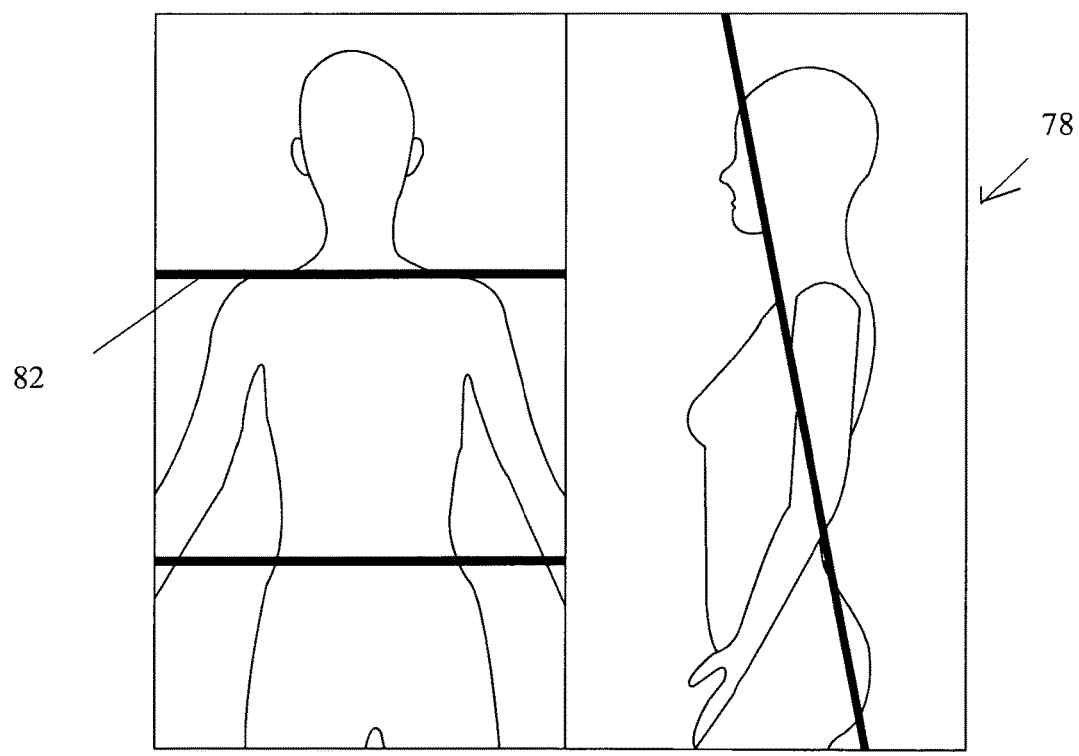

Now referring to FIGS. 3A and 3B, screenshots exemplifying the optional user interface 78 of software product 54 are provided. In FIG. 3A, an information form page 80 that displays information about the positions and locations of the lasers is automatically provided through photograph transmission means 62. A practitioner may also enter additional information, such as gender, height, weight, and other notes, about the patient on this screen. In FIG. 3B, a depersonalized human illustration 82 is superimposed on the photograph of the grid sheet 16 with lasers specific to the patient. Providing a human illustration gives reference to the laser indications but is depersonalized from using a depiction of the actual patient. As used herein "depersonalized" means that only general characteristics of the human form are indicated, with no features or characteristics of a specific individual or patient indicated.

Although the present invention has been described in considerable detail with reference to certain preferred versions thereof, other versions would be readily apparent to those of ordinary skill in the art. Therefore, the spirit and scope of the description should not be limited to the description of the preferred versions contained herein.

I claim:

1. A posture assessment system comprising:
    a base comprising a center portion, a base left side, and a base right side;
    a frame extending perpendicularly upward from said base, said frame comprising:
        a frame left side extending upward from said base left side;
        a frame right side extending upward from said base right side;
        a top side connecting said frame right side and said frame left side; and
        an arm extending perpendicularly outward from said top side, such that said arm is parallel to said base, wherein said arm comprises an end disposed at a distance from said top side;
    a grid sheet hanging from said top side of said frame such that a width of said grid sheet is disposed entirely between said frame left and right sides;
    at least an upper and lower left side laser disposed on said frame left side, wherein each of said upper and lower left side lasers comprise left side laser adjustment means;
    at least an upper and lower right side laser disposed on said frame right side, wherein each of said upper and lower right side lasers comprise right side laser adjustment means;
    at least one top side laser disposed on said top side, wherein said at least one top side laser comprises top side laser adjustment means;
    a camera disposed on said end of said arm;

photograph transmission means for transmitting at least one photograph taken by said camera; and a downloadable software program comprising software means for:

receiving the at least one photograph taken by said camera;

receiving practitioner input;

superimposing the at least one photograph onto a depersonalized human image with normal posture; and producing a posture assessment.

2. The posture assessment system as claimed in claim 1, wherein:

said frame left side comprises a top and said frame right side comprises a top;

said top side comprises a first crossbar extending between said tops of said frame right and left sides and a second crossbar extending between said frame right and left sides below said first crossbar;

said arm extends from said first crossbar; and said top laser is disposed on said second crossbar.

3. The posture assessment system as claimed in claim 2, wherein said second crossbar is disposed zero to three inches below said first crossbar.

4. The posture assessment system as claimed in claim 1, wherein:

said left side laser adjustment means comprise means for moving said upper and lower left side lasers vertically along said left side of said frame to a location on said left side;

said right side laser adjustment means comprise means for moving said upper and lower right side lasers vertically along said right side of said frame to a location on said right side; and said top side laser adjustment means comprise means for:

moving said top side laser horizontally along said top side of said frame; and angling said top side laser through a range with respect to said top side of said frame.

5. The posture assessment system as claimed in claim 1, wherein said software program further comprises software means for commanding said camera to take the at least one photograph.

6. The posture assessment system as claimed in claim 1, wherein:

said photograph transmission means comprise physical wires extending from said camera; and said physical wires of said photograph transmission means are disposed such that the at least one photograph taken by the camera are received by said software product.

7. The posture assessment system as claimed in claim 6, further comprising a hub into which at least said physical wires of said photograph transmission means meet.

8. The posture assessment system as claimed in claim 1, wherein said photograph transmission means are wireless and said software product receives the at least one photograph taken by the camera wirelessly.

9. The posture assessment system as claimed in claim 1, further comprising switches for turning said upper and lower left side lasers, said upper and lower right side lasers, and said top laser on and off.

10. The posture assessment system as claimed in claim 1, wherein said software product comprises further means for commanding said upper and lower left side lasers, said upper and lower right side lasers, and said top laser to turn on and off.

11. The posture assessment system as claimed in claim 1, wherein said frame right and left sides comprise a height of at least six feet.

12. The posture assessment system as claimed in claim 1, wherein said software product comprises further means for providing a user interface.

13. The posture assessment system as claimed in claim 12, wherein said user interface displays the at least one photograph superimposed onto the depersonalized human image with normal posture.

14. The posture assessment system as claimed in claim 12, wherein said user interface comprises an information form page where information about a specific patient is input by at least the practitioner.

15. The posture assessment system as claimed in claim 1, wherein said camera comprises camera adjustment means for adjusting an angle of said camera with respect to said grid sheet.

16. The posture assessment system as claimed in claim 1, further comprising a device for measuring an electrical impedance of a patient.

17. The posture assessment system as claimed in claim 16, wherein said device for measuring the electrical impedance of the patient is a handle extending from one of a group consisting of said frame and said base, wherein the electrical impedance of the patient is measured when the patient grasps said handle by a hand of the patient.

18. The posture assessment system as claimed in claim 1, wherein said base comprises a scale that measures a weight of a patient.

19. The posture assessment system as claimed in claim 1, wherein said photograph transmission means for transmitting at least one photograph taken by said camera also transmit locations of said upper and lower left side lasers, said upper and lower right side lasers, and said top laser.

20. The posture assessment system as claimed in claim 1, further comprising laser transmission means for transmitting information about locations of at least said first and second left side lasers, said first and second right side lasers, and said top side laser, and the angle of said top side laser, and wherein said software program further comprises software means for receiving the locations of said first and second left side lasers, said first and second right side lasers, and said top side laser, and the angle of the top side laser.

21. The posture assessment system as claimed in claim 16, further comprising electrical impedance transmission means for transmitting the electrical impedance of the patient, and wherein said software program further comprises software means for receiving the electrical impedance of the patient.

22. The posture assessment system as claimed in claim 18, further comprising patient weight transmission means for transmitting the weight of the patient, and wherein said software program further comprises software means for receiving the weight of the patient.

23. The posture assessment system as claimed in claim 1, wherein said camera comprises video capabilities to aid in assessing a range of motion of a patient.

* * * * *